United States Patent [19]

Patterson et al.

[11] 4,180,562

[45] Dec. 25, 1979

[54] GLUTARALDEHYDE POLYMERIZED RAGWEED ANTIGEN E PREPARATION FOR TREATMENT OF ALLERGIC PATIENTS SENSITIVE TO RAGWEED POLLEN

[75] Inventors: Roy Patterson, Wilmette, Ill.; Floyd C. McIntire, Denver, Colo.

[73] Assignees: Northwestern University, Evanston; Abbott Laboratories, North Chicago, both of Ill.

[21] Appl. No.: 879,966

[22] Filed: Feb. 21, 1978

Related U.S. Application Data

[63] Continuation-in-part of Ser. No. 788,049, Apr. 15, 1977, abandoned, Continuation of Ser. No. 358,223, May 8, 1973, abandoned.

[51] Int. Cl.² ............................................. A61K 39/36
[52] U.S. Cl. .................................. 424/91; 260/112 R
[58] Field of Search ........................ 260/112 R; 424/91

[56] References Cited

U.S. PATENT DOCUMENTS

| | | | |
|---|---|---|---|
| 3,794,630 | 2/1974 | Mullan et al. .................... | 260/112 R |
| 3,983,229 | 9/1976 | Relyveld .............................. | 424/91 |
| 4,070,455 | 1/1978 | Green et al. ......................... | 424/91 |

OTHER PUBLICATIONS

Chem. Abstracts, vol. 64, 1966, 14760b-d, Robbins et al.
Chem. Abstracts, vol. 74, 1971, 123063h, Griffiths et al.
Immunochemistry, 6, pp. 53-66, (1969), Avrameas et al.
Int.-Arch. Allergy, 41, pp. 778-789, (1971), Tannenbaum et al.
J. Immunol., 110, pp. 1402-1412, (1973), Patterson et al.
Biochemistry, 1, pp. 709-720, (1962), King et al.
Biochemistry, 3, pp. 458-468, (1964), King et al.
Immunochemistry, 7, pp. 581-585, (1970), Sachs et al.
J. of Immunology, vol. 102, No. 2, 1969, pp. 457-465, Habeeb.
Immunochemistry, vol. 6, 1969, pp. 43-52, Avrameas.

*Primary Examiner*—Howard E. Schain
*Attorney, Agent, or Firm*—Tilton, Fallon, Lungmus & Chestnut

[57] ABSTRACT

The preparation of this invention comprises ragweed antigens polymerized with glutaraldehyde which are composed essentially of water-soluble polymers of molecular weights from 200,000 to 20,000,000.

2 Claims, No Drawings

GLUTARALDEHYDE POLYMERIZED RAGWEED ANTIGEN E PREPARATION FOR TREATMENT OF ALLERGIC PATIENTS SENSITIVE TO RAGWEED POLLEN

GRANT REFERENCE

The invention described herein was made in the course of work under a grant from the Department of Health, Education, and Welfare.

CROSS-REFERENCES

This application is a continuation-in-part of co-pending application Ser. No. 788,049, filed April 15, 1977, and now abandoned, which in turn was a continuation of application Ser. No. 358,223, filed May 8, 1973, and now abandoned.

BACKGROUND AND PRIOR ART

In the United States one of the most common allergies is to ragweed pollen. Allergic patients sensitive to ragweed have been immunized by repeated injections of ragweed antigen. The injections are given subcutaneously. Because patients are allergic to the injected antigens, it has been necessary in clinical practice to administer a large number of small but increasing doses over an extended period of time. Further, even with this regimen, some patients cannot tolerate the injections because of their very high sensitivity to the injected ragweed antigens. It has therefore been desired to provide a means for increasing the effectiveness of preparations for use in treating ragweed sensitive patients. More specifically, it has been desired to reduce the allergenicity (IgE mediated reactions) of such preparations, while maintaining or improving the immunogenicity (ability to induce IgG antibody). Optimally, the patient would be immunized by giving a few large doses of the ragweed antigen, and the immunity would be maintained for several weeks or months without the need for additional injections. Heretofore, however, these objectives have not been achieved.

In the U.S. Pat. No. 3,794,630, there is disclosed a method for reacting protein allergenic extracts with dialdehydes such as glutaraldehyde. The resultant products which are said to be substantially water-insoluble are claimed to provide reduced allergenicity relative to the untreated allergen. The examples disclose the preparation of such water-insoluble polymerized products from extracts of Cocksfoot pollen and timothy pollen. There is no example or other reference to ragweed pollen.

SUMMARY OF INVENTION

According to the present invention, ragweed antigens, such as ragweed antigen E, are polymerized with glutaraldehyde to produce water-soluble polymers of specified molecular weight ranges. After the polymerization reaction, the mixed polymers are fractionated in aqueous solutions. For purpose of the present invention, it is particularly important that polymers having molecular weights of less than 200,000 are removed, as well as any residual unpolymerized ragweed antigens. Very large polymers, such as those above 20,000,000 molecular weight, may also be removed and this is preferred. The resulting product is thereby composed essentially of water-soluble polymers of ragweed antigens of molecular weights from 200,000 1 to 20,000,000, and the preparations are substantially free of unpolymerized ragweed antigens and polymers thereof having molecular weights of less than 200,000.

The preparations of the present invention are immunogenic, providing at least as good and usually somewhat better immunogenicity (ability to produce IgG antibody response) than the unpolymerized ragweed antigens. Moreover, the preparations are characterized by markedly reduced allergenicity (ability to produce allergic response), not only with respect to unpolymerized ragweed antigens but also as compared with preparations containing polymerized ragweed antigens of less than 200,000 molecular weight. The invention therefore makes possible an improved therapy with fewer injections. For example, the required number of injections given safely may be reduced in clinical practice to as little as 1/10 the injections presently required to reach maintenance dose using current therapy with unpolymerized ragweed antigens.

DETAILED DISCLOSURE

Ragweed pollen contains several antigens, the principal antigenic factor being identified as ragweed antigen E. The present invention may be practiced either with mixed ragweed antigens or with isolated antigen E. For commercial purposes, the mixed antigens are preferred because they are less expensive to prepare. In general, the ragweed pollen is extracted with other aqueous solvent to obtain the ragweed antigens, which, if desired, can be further purified. The extracted purified antigenic factors are then reacted with glutaraldehyde to form a mixture of polymers. The reaction can be carried out at moderate temperatures, such as at temperatures from 20° to 30° C., using an aqueous solution of the glutaraldehyde to treat the ragweed antigens. A suitable concentration of glutaraldehyde is 0.625 ml of 1:50 glutaraldehyde for 10 mg of ragweed antigen. Reaction times of 3 to 5 hours are suitable.

After the polymerization has been carried out as far as desired, the polymerization reactions may be terminated. For example, further polymerization can be stopped by adding glycine, or similar reagent. The polymerization should not be carried to the point where any substantial amount of water insoluble polymers are produced. If some water-insoluble polymeric material is present, this should be removed, such as by filtration. The solution of water-soluble polymers is then fractionated, such as by chromatographic separation. The adsorbents and conditions are selected so that in one separation the polymers having molecular weights above 20,000,000 are removed, and in a prior or subsequent separation, the polymers having molecular weights of less than 200,000 are removed. There is thereby obtained an aqueous solution of glutaraldehyde polymerized ragweed antigens having molecular weights of from 200,000 to 20,000,000, and being substantially free of unpolymerized ragweed antigens, and polymers thereof having molecular weights of less than 200,000. This product may be recovered in solid form by evaporation of the water, or by precipitation with ammonium sulfate. The solid product, being water-soluble, may then be redissolved in a suitable aqueous carrier for subcutaneous injection (viz. buffered normal saline). It will be understood that the preparation should be sterilized before administration, either before or after being combined with the aqueous vehicle, and that the preparation is in aqueous solution when administered.

Initial studies of polymerized ragweed antigens defined certain antigen characteristics. These included the demonstration that all antigenic determinants of ragweed antigen E were present on the polymerized material. Two high molecular weight fractions were prepared, a polymerized ragweed antigen with molecular weights ranging approximately between 200,000 and 4,000,000 designated low molecular weight polymerized ragweed (LMW-P-RW), and a high molecular weight polymerized ragweed (HMW-P-RW) with molecular weights ranging between 4,000,000 and 20,000,000. These two preparations produced immune responses in guinea pigs and rabbits. Further studies were done to evaluate the characteristics of the polymerized ragweed antigens including those which might apply to potential therapeutic usefulness in therapy of human patients with ragweed pollenosis. The procedures are illustrated by the following examples.

EXAMPLE 1

Dwarf ragweed (*Ambrosia elatior*) was fractionated by the method of King and Norman, Biochemistry, 3: 458 (1964). The fraction IV obtained by ammonium sulfate precipitation, diethylaminoethyl cellulose and Sephadex chromatography was further fractionated through triethylaminoethyl cellulose and Fraction IVC containing nearly 100 percent Antigen E was removed and used for certain studies. AgE has a molecular weight of about 38,000. The remainder of Fraction IV, containing Fractions IVA, IVB, and IVD were combined. This pool of Fraction IV minus IVC was calculated to contain about 60 percent ragweed antigen E and was used for polymerization by glutaraldehyde treatment. Fraction IVC is designated AgE and Fraction IV minus IVC is designated RW. RW was later shown to be about 30 percent AgE by immunoassay.

All preparations of RW were evaluated by measuring optical density at 280 nm with a Beckman DU spectrophotometer. One O.D. unit was estimated to be approximately 1 mg of protein per ml and expressed as such for subsequent immunologic studies.

EXAMPLE 2

RW, obtained by the method of Example 1, comprising mixed ragweed antigens with a content of about 30% antigen E, was treated with glutaraldehyde using the method of Sachs and Winn, Immunochemistry, 7: 581 (1970). Polymerization was done at room temperature for 4 hours. For 10 mg of RW, 0.625 ml of 1:50 glutaraldehyde was used. 10 to 30 mg of the RW protein was used for glutaraldehyde treatment on each occasion that polymerized RW (P-RW) was prepared. Preparations of P-RW were fractionated using Sephadex or Sepharose (Pharmacia Fine Chemicals AB, Uppsala, Sweden). Sephadex G-200, or Sepharose 6B, 4B or 2B were used for various fractionations using 40×2.5 cm columns. The Sephadex and Sepharose columns and protein solutions were equilibrated with a 0.1 M TRIS, 0.15 M NaCl buffer, pH 7.9. The protein content of the eluates was determined by the optical density at 280 nm using a Beckman DU spectrophotometer. Dextran Blue 2000 was used as a molecular marker in various columns to aid in determination of excluded and included fractions. Polymerized material having a molecular weight in excess of 200,000 was thereby obtained.

When RW is treated with glutaraldehyde and the resultant P-RW was fractionated through a Sephadex G-200 column, the major portion of the glutaraldehyde treated RW protein appears in a defined peak. This material in the exclusion volume of the Sephadex G-200 has a molecular weight in excess of 200,000. Further fractionation of the polymerized material using a column of Sepharose 6B gave two protein fractions. These were a sharp peak containing protein in the exclusion volume of Sepharose 6B and a broad shoulder in the inclusion volume. The sharp peak is considered to be composed of polymerized ragweed with a molecular weight in excess of 4,000,000 termed high molecular weight polymerized ragweed (HMW-P-RW) (Pool I). The second, diffuse protein fraction is considered to have a spectrum of material with molecular weights ranging from 200,000 to 4,000,000 (LMW-P-RW) (Pool II). When Pool I was fractionated through a Sepharose 4B column, 2 peaks were obtained. The first peak in the exclusion volume of Sepharose 4B, was considered to have a molecular weight in excess of 20,000,000 and the second peak in the inclusion volume of Sepharose 4B, was considered to have a range of molecular weights from 4,000,000 to 20,000,000. Both HMW-P-RW and LMW-P-RW were entirely water soluble.

EXAMPLE 3

Subsequent to the above studies showing the various ranges of molecular weights of polymerized ragweed resulting from gluaraldehyde treatment of ragweed, a standard procedure for evaluation of the polymerized material was developed. These studies used the addition of $^{125}$I AgE to RW in order to examine the effect of glutaraldehyde treatment on a major antigen of RW. The $^{125}$I AgE is not, of course used in the materials prepared for human use. The RW with added $^{125}$I AgE was treated with glutaraldehyde and fractionated through Sepharose 6B. The radioactive protein ($^{125}$I AgE) included in the Sepharose 6B had molecular weight ranges less than 4,000,000. The included Sepharose 6B fractions were fractionated through Sephadex G-200 and the excluded fractions had a molecular weight of more than 200,000. These studies showed the $^{125}$I AgE in RW was polymerized and the polymers of LMW-P-RW had molecular weight ranges of 200,000 to 4,000,000. The excluded fractions from Sepharose 6B (molecular weight more than 4,000,000) were fractionated through Sepharose 4B. The $^{125}$I AgE was found in the included fractions. These included fractions, termed HMW-P-RW, had a molecular weight range of 4,000,000 to 20,000,000. These procedures were done because of the variable degree of polymerization which could occur during the preparation of P-RW and to define the polymerization process with a major radiolabelled antigen.

The preparations of RW material polymerized with glutaraldehyde treatment showed a wide range of molecular weights as demonstrated by the elution patterns of the Sepharose 6B, 4B and Sephadex G-200 fractionations. Although slight variability in the patterns was observed with different batches, there was good reproducibility in more than 5 individual polymerization experiments. The yield of polymerized material was over ninety percent as estimated from the optical density yield of the polymerized materials and the polymerized materials remained soluble during the course of these experiments. The products were water-soluble polymers ranging in molecular weights from below 200,000 to above 20,000,000. Previous reports of glutaraldehyde treatment of other proteins (Sachs et al., Immunochemistry, 8: 58 (1970) demonstrated that less than one percent of the proteins were uncoupled. In evaluations of RW polymer stability, the polymer was shown to be stable during standard storage conditions up to 6 months.

The RW treated with glutaraldehyde retained its antigenicity and reacted with all antibody in antiserum prepared against unpolymerized RW. Although the polymerized ragweed preparations could react with all antibody against RW antigen in an antiserum, as demonstrated by neutralization experiments, increasing concentrations of the polymerized preparations were required to accomplish this in proportion to the molecular size of the polymers.

The antibody responses in guinea pigs immunized with RW, LMW-P-RW and HMW-P-RW demonstrated that all preparations produced antibody responses but these were not evident until after tertiary immunization even with a technique as sensitive as the ammonium sulfate isotope labeled antigen technique used for detection. This lack of response to primary and secondary stimulation was not unexpected as good antibody responses to ragweed antigens generally require repeated antigen administration. The results of antibody responses in guinea pigs to the 3 RW materials demonstrated that the polymerized materials are at least as antigenic in this species as RW and that the LMW-P-RW is probably the most antigenic of the 3 molecular species.

Results of immunization experiments with rabbits were similar and also suggest that immune response to injection with LMW-P-RW is at least as good as, and probably superior, to the RW or HMW-P-RW.

Glutaraldehyde polymerized preparations of ragweed with a significant portion of antigen E, the major antigen of ragweed pollen, have certain characteristics. These include: complete reactivity of the polymerized ragweed with antibody against the monomeric form, no significant formation or exposure of new antigenic determinants during polymerization, antigenicity which is at least that of the native antigen E, reactivity with IgE antibody, and a marked diminution of allergic reactivity on a weight basis, as demonstrated by histamine release from cells from allergic humans in vitro and allergic skin reactions to RW sensitive humans. The results suggest the potential usefulness of these preparations for human allergen immunotherapy with antigen E and possibly other purified inhalant antigens. This potential use is based on the persistent and probably enhanced antigencity of polymerized ragweed preparations combined with their diminished reactivity with IgE sensitized mast cells and their diminished rate of absorption from locally injected sites as compared with the native antigen E monomer.

EXAMPLE 4

Pollens were obtained from Hollister-Stier Laboratories (Spokane, Washington). Giant and short ragweed pollens were used. These pollens were defatted with ethyl ether several times. The defatted pollen grains were extracted with isotonic phosphate buffered saline, pH 7.2 (PBS) at 4° C. for 24 hours. The preparation was centrifuged at 17,000×G for 1 hr and the precipitate was discarded. Proteins in the crude extract were precipated with ammonium sulfate at 90 percent saturation level. Resulting precipitate was dissolved in PBS, and dialyzed at 4° C. against PBS until free of ammonium sulfate. Further purification of extract was done by chromatography on a Sephadex G-15 column. The excluded portion of Sephadex G-15 was the monomer ragweed (MRW).

For each 10 mg MRS, 0.625 ml 1:50 glutaraldehyde (25% grade II, Sigma Chemical Company) was added. The polymerization of MRW was carried out at room temperature for 4 hours using a magnetic stirrer. Then glycine was added to stop further polymerization. The glutaraldehyde treated mixture was fractionated on a Sepharose 4B (Pharmacia) column to remove polymers above 20,000,000 daltons and the fractions included by the Sepharose 4B column were combined. The polymerized ragweed (PRW) of below 20,000,000 daltons was placed in a dialysis bag and concentrated by evaporation to 4 cc and dialyzed free of excess glutaraldehyde and glycine. The PRW was then applied to a Sephadex G-200 (Pharmacia) column. The fractions excluded (above 200,000 daltons) or included (below 200,000 daltons) by the Sephadex G-200 were combined and stored at −20° C. until use. Preparation I thus prepared contained polymers within the range from 200,000 to 20,000,000, while Preparation II contained polymers 200,000 molecular weight. Before human use, they were dialyzed for 48 hrs against phosphate buffered 0.15 M NaCl, pH 7.35, containing 0.5% phenol.

RW preparations were sterilized by filtration using a filter unit (0.20 micron plain membrane, Nalge, Sybron Corp., N.Y.). They were cultured for sterility by the microbiology laboratories of Northwestern Memorial Hospital at 48 hrs and following 2 weeks of culture. Preparations were proved to be sterile before use in the human studies reported below.

Cutaneous titration (human). Three ragweed sensitive subjects were tested by intracutaneous injection of 0.02 ml of serial 10-fold dilutions of each preparation. Reactions were graded 1 to 4 plus positive and the endpoint titration was the highest dilution giving a wheal and erythema reaction. The results are summarized in the following Table A.

TABLE A

| Polymerized Ragweed Antigens (molecular weight) | Allergenic Responses of Three Ragweed Sensitive Subjects (endpoint dilution titers*) | | |
|---|---|---|---|
| | Subject A | Subject B | Subject C |
| I. 200,000-20,000,000 | $10^{-2}$ | negative | negative |
| II. below 200,000 | $10^{-8}$ | $10^{-8}$ | $10^{-5}$ |
| III. combined I & II | $10^{-3}$ | $10^{-5}$ | $10^{-1}$ |

*The number recorded is the highest serial 10-fold dilution giving a positive wheal and erythema reaction.

The foregoing results demonstrate that ragweed allergens treated with glutaraldehyde have dramatically reduced allergenicity in the molecular weight range of 200,000 to 20,000,000. On the other hand, allergenicity is retained in the lower molecular weight polymers (below 200,000) even though they have been subjected to the identical treatment with glutaraldehyde. The difference in degree of allergenicity as determined by cutaneous endpoint titration varied from at least $10^5$ to $10^8$. The reduced allergenicity of Preparation I was not at the expense of immunogenicity, as has already been demonstrated.

EXAMPLE 5

Using a similar procedure of that described in Example 4 ragweed antigens (King's IV–IVC) were polymerized with glutaraldehyde, and subjected to chromatographic separation to prepare a polymerized product containing polymers within the molecular weight range from 200,000 to 20,000,000. This preparation (PRW) was compared with the unpolymerized ragweed antigens (MRW) with respect to the degree of allergenicity. Three ragweed sensitive human subjects were tested by intracutaneous injection of 0.02 ml of serial 10-fold dilutions of both PRW and MRW. Reactions were graded 1 to 4 plus positive, and the endpoint titration was the highest dilution given a wheal and erythema reaction. The results are reported below in Table B and show that in this experiment the polymer was 100 to 1000 fold less allergenic.

TABLE B
COMPARATIVE ALLERGENICITY OF POLYMERIZED AND UNPOLYMERIZED RAGWEED ANTIGENS

| Concentration of RW tested (ug/ml)* | Subject 1 | | Subject 2 | | Subject 3 | |
|---|---|---|---|---|---|---|
| | MRW | PRW | MRW | PRW | MRW | PRW |
| 50 | ND | ND | ND | ND | ND | +++ |
| 5 | ND | +++ | ND | ND | ND | — |
| 0.5 | ND | — | ND | +++ | +++ | — |
| 0.05 | +++ | — | ++++ | — | ++ | — |
| 0.005 | ++ | — | ++ | — | — | — |
| 0.0005 | — | — | — | — | — | — |

*based on optical density at 280 nm using a Gilford 250 spectrophotometer.
Abbreviations: RW, ragweed antigen; MRW, unpolymerized ragweed antigens; PRW, polymerized ragweed (200,000–20,000,000 daltons); ND, not done.

EXAMPLE 6

It can be demonstrated that RW antigens are not only incorporated in the RW Polymers of this invention, but once incorporated, that they are also effective immunogens. The following study is illustrative. Serum samples from 2 patients immunized with RW polymer were studied. Pure RW antigens used included Antigen E (described above), Ra3 and Antigen K, the latter two being obtained from the National Institutes of Health. The results are shown in Table C and demonstrate significant IgG antibody responses against the available RW antigens.

TABLE C

| | Immune response in ragweed allergic humans treated with polymerized RW. | | | |
|---|---|---|---|---|
| | Percent increase+ in IgG antibody* activity | | | |
| Subject | Crude Ragweed | AgE | AgK | Ra3 |
| 1 | 330 | 390 | 200 | 70 |
| 2 | 700 | 800 | 300 | 4700 |

$+100 \times \frac{\text{Postreatment IgG binding activity} - \text{Pretreatment binding activity}}{\text{Pretreament binding activity}}$

*Determined by solid phase radioimmunoassay using polystyrene tubes

EXAMPLE 7

(a) Clinical trials with glutaraldehyde polymerized RW (molecular weight 200,000 to 4,000,000) compared with monomeric RW showed that polymerized ragweed antigens was as effective as monomeric RW in control of symptoms ragweed allergic rhinitis as evaluated by symptom score indices. The polymerized RW produced fewer allergic reactions during the immunization process.

(b) Clinical trials with glutaraldehyde polymerized RW (Molecular weight 200,000 to 20,000,000) compared with monomer RW showed that the polymer RW was as effective in control of ragweed allergic rhinitis as monomer. IgG response to AgE was similar. Allergic reactions to the preparations during immunization treatment were markedly reduced in the polymer group.

These studies showed that polymer RW (molecular weight 200,000 to 20,000,000) was at least as effective in treatment of ragweed allergic rhinitis as monomeric RW.

EXAMPLE 8

Immunization with the polymerized RW of this invention significantly reduced allergic reactions during treatment. Consequently, as shown by the following studies, the number of injections of polymer RW can be markedly reduced, as compared with currently available ragweed immunization therapy. The results are reported in Table D.

| | Aqueous (monomeric) Ragweed | Polymer Ragweed |
|---|---|---|
| Starting dose[a] | 2.5 P.N.U.[b] | 500 P.N.U. |
| Maintenance dose[a] | 2500.0 P.N.U. | 2500 P.N.U. |
| Number of injections to reach maintenance dose[a] | 30–50 | 3–5[c] |

[a]Starting and maintenance doses may vary with practicing allergist as may the rate of progression of dose. These are procedures which usually produce no local or systemic allergic reactions. All patients do not tolerate this schedule.
[b]P.N.U.: Protein nitrogen units. One P.N.U. contains 10 ng protein nitrogen. P.N.U. is a commonly used expression of allergen potency. A 1:50 weight per volume extract of ragweed pollen contains approximately 10,000 P.N.U.
[c]25 typical ragweed allergic patients have received this therapy.

We claim:

1. A preparation for treatment of allergic patients sensitive to ragweed pollen, comprising ragweed antigen E polymerized with glutaraldehyde and being composed essentially of water-soluble polymers thereof of molecular weights from 200,000 to 20,000,000, said preparation being substantially free of unpolymerized ragweed antigen E and polymers thereof having molecular weights of less than 200,000.

2. A method of treating an allergic patient sensitive to ragweed pollen to alleviate the allergy, comprising administering to said patient by intracutaneous injection ragweed antigen E polymerized with glutaraldehyde and being composed essentially of water-soluble polymers thereof of molecular weights from 200,000 to 20,000,000, said preparation being substantially free of unpolymerized ragweed antigen E and polymers thereof having molecular weights of less than 200,000.

* * * * *